United States Patent [19]
Stockley et al.

[11] Patent Number: 6,159,728
[45] Date of Patent: *Dec. 12, 2000

[54] RNA BACTERIOPHAGE-BASED DELIVERY SYSTEM

[75] Inventors: Peter George Stockley, Ilkley, United Kingdom; Robert Allan Mastico, Braintree, Mass.

[73] Assignee: BTG International Limited, London, United Kingdom

[*] Notice: This patent is subject to a terminal disclaimer.

[21] Appl. No.: 08/360,694

[22] PCT Filed: Jun. 25, 1993

[86] PCT No.: PCT/GB93/01338

§ 371 Date: Jan. 24, 1995

§ 102(e) Date: Jan. 24, 1995

[87] PCT Pub. No.: WO94/00588

PCT Pub. Date: Jan. 6, 1994

[30] Foreign Application Priority Data

Jun. 26, 1992 [GB] United Kingdom .................. 9213601

[51] Int. Cl.⁷ .............................. A01N 63/00; C12N 7/00; C12N 7/01
[52] U.S. Cl. ................. 435/320.1; 424/93.2; 424/93.6; 435/375; 435/455; 435/456; 435/471; 435/472
[58] Field of Search .......................... 424/89, 93.2, 93.6; 514/44; 435/320.1, 455, 456, 471, 472, 375

[56] References Cited

U.S. PATENT DOCUMENTS 5,298,244 3/1994 Redman et al. .......................... 424/89

FOREIGN PATENT DOCUMENTS

| 2 257 431 | 1/1993 | United Kingdom . |
|---|---|---|
| WO 87/06261 | 10/1987 | WIPO . |
| WO 92/03537 | 3/1992 | WIPO . |
| WO 92/06180 | 4/1992 | WIPO . |
| WO 92/13081 | 8/1992 | WIPO . |

OTHER PUBLICATIONS

Beckett et al., "Roles of operator and non-operator RNA sequences in bacteriophage R17 capsid assembly", J. Mol. Biol. 204: 939–947, Dec. 1988.

Gorden et al, Gene Therapy using Retroviral Vectors, Current Opinion in Biotechnology5:611–16, 1994.

Etienne–Julan et al, The efficiency of cell targeting by recombinant retroviruses depends on the nature of the receptor and the composition of the artificial cell–virus linker, Journal of General Virology, 73:3251–3255, 1992.

Rodriguiz et al, Vectors: A Survey of molecular cloning Vectors and their use, p495–97, 1987.

S.J. Talbot, et al. "Use of synthetic oligoribonucleotides . . ." Nucleic Acids Research, vol. 18 No. 12 (Jun. 25, 1990), pp. 3521–3528.

*Primary Examiner*—Scott D. Priebe
*Attorney, Agent, or Firm*—Nixon & Vanderhye

[57] ABSTRACT

A delivery system, especially for delivery to targeted sites in the human or animal body, comprises capsids of the coat protein amino acid sequence of phage MS-2 or related phage, or a modification thereof which retains capsid-forming capability, and at least some of the capsids enclosing a moiety foreign to the genome of MS-2 or related phage.

16 Claims, 8 Drawing Sheets

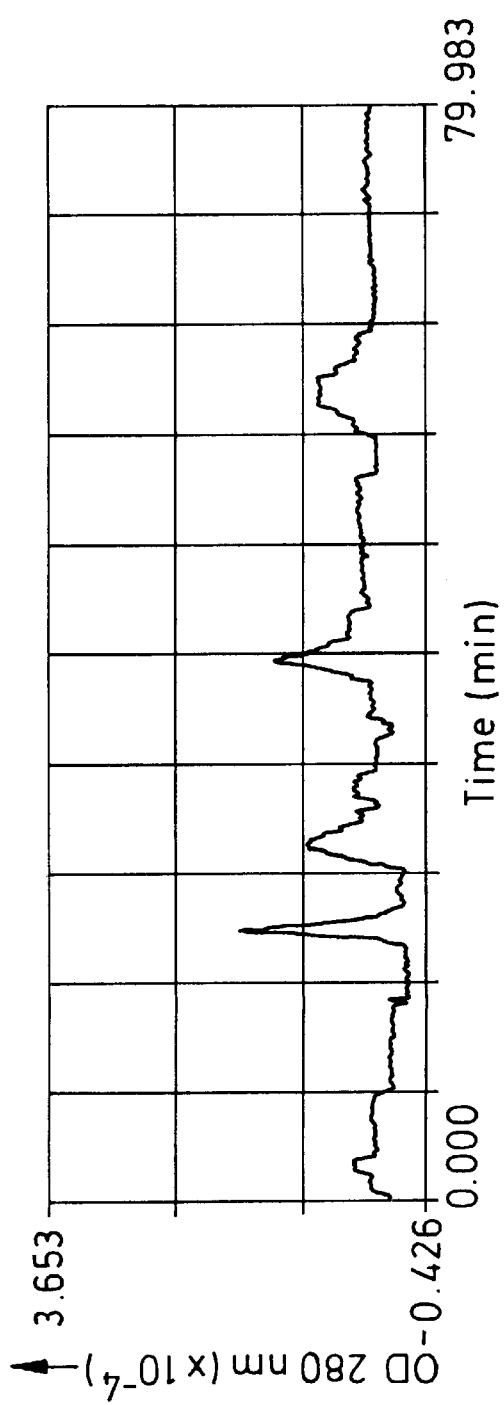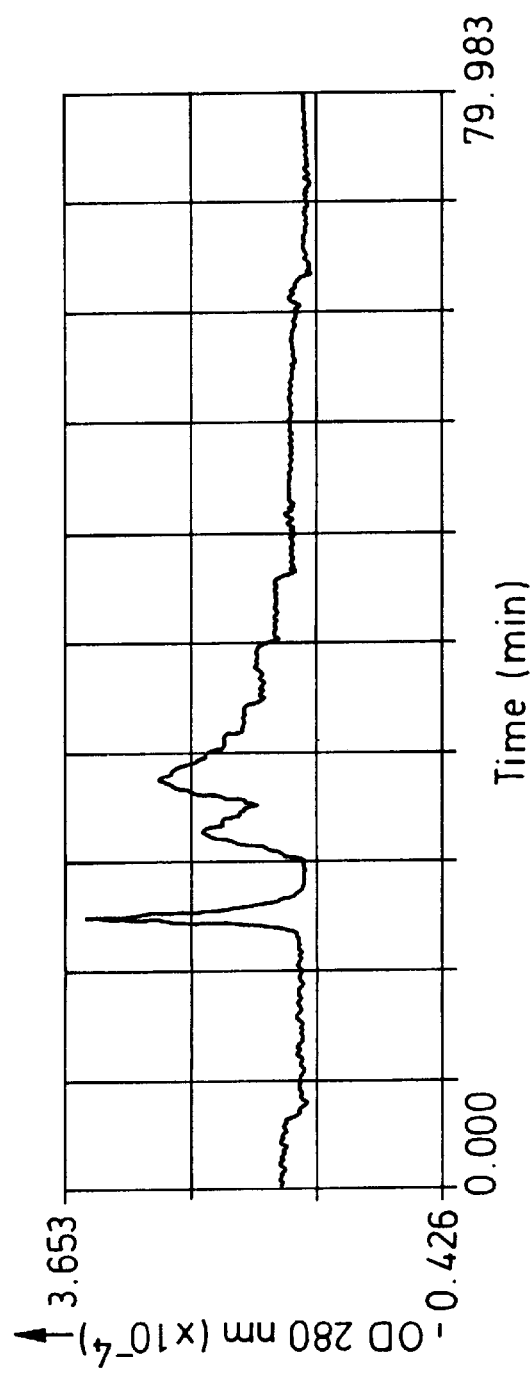

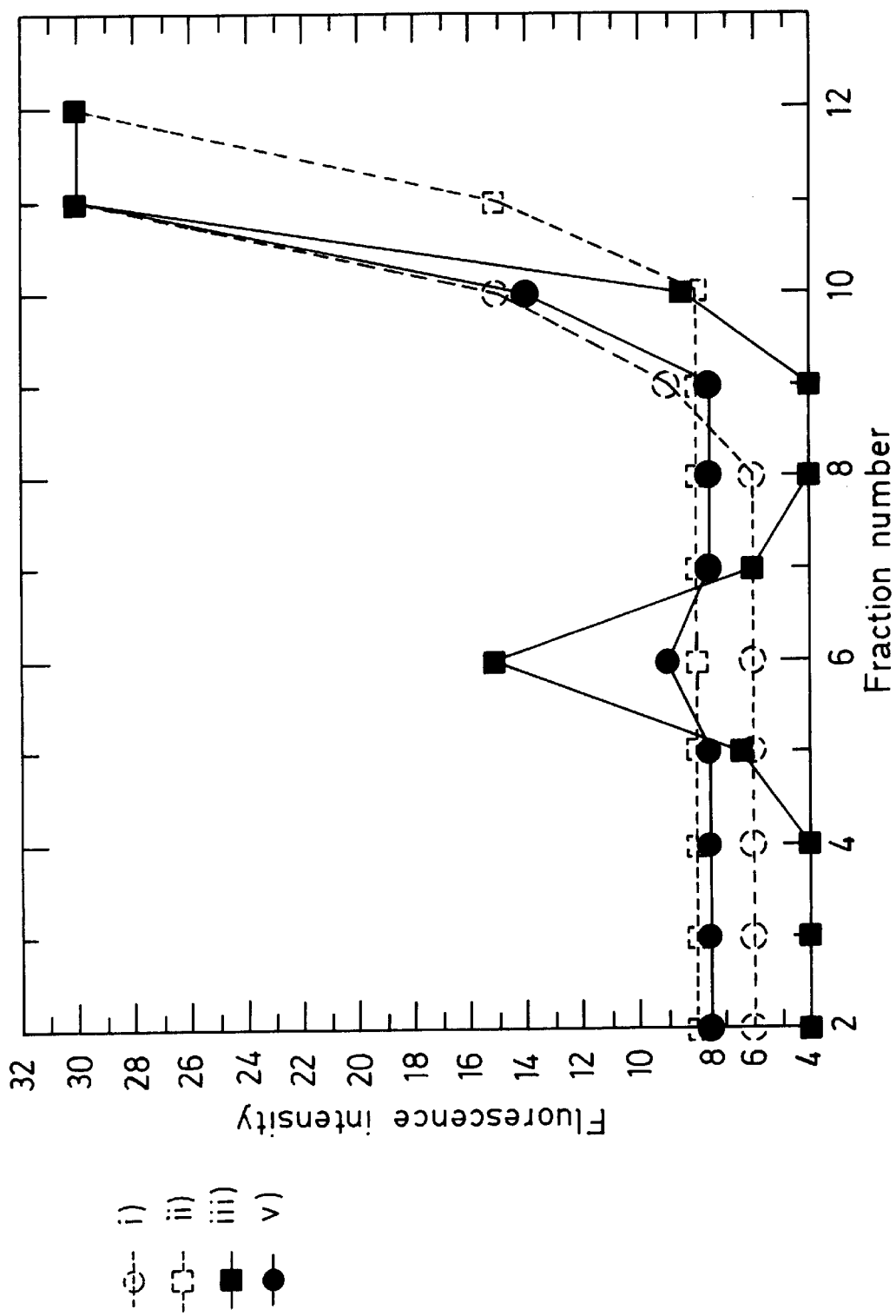

RNA BACTERIOPHAGE-BASED DELIVERY SYSTEM

This invention relates to a protein-based delivery system and is particularly directed to the delivery of encapsidated foreign moieties, especially to targeted sites in the human or animal body.

There is increasing interest in the targeting of foreign moieties to the sites in the body where their activity is required. Thus it is important that drugs, particularly those having undesirable side effects, are delivered to the site where they are to act. Many other molecular species require to be delivered in a site specific manner, often to particular cells, for example polynucleotides (anti-sense or ribozymes), metabolic co-factors or imaging agents. One such system has been described by Wu et al., J. Biol. Chem., 263, 14621–14624 and WO-A-9206180, in which a nucleic acid useful for gene therapy is complexed with polylysine linked to galactose which is recognised by the asialoglycoprotein receptors on the surface of cells to be targeted. However, there are many occasions, such as in the delivery of a cytotoxic drug, when it would not be satisfactory to use a delivery system in which the moiety to be delivered is so exposed. There is therefore a need to develop alternative delivery systems which have the flexibility to target a wide range of biologically active foreign moieties.

Co-pending UK patent applications no. 9114003.8 and 9201372.1 describe the modification of the coat protein of phage MS-2 as a presentation system for epitopic species, which may be included in a modified coat protein sequence or attached to the coat protein via a cysteine residue and optional further spacer. These applications relied on the ability of the coat protein of MS-2 and similar phages to be cloned and expressed in a bacterial host such as E. coli as largely RNA-free empty phage particles. Romaniuk et al., (1987), Biochemistry 26, 1563–1568 have studied the relationship between the MS-2 coat protein and the RNA genome. It is apparent that, although RNA-free coat protein assemblies can be produced in E. coli, capsid formation in natural infections is triggered by coat protein interaction with a 19 base stem-loop (translational operator) in the RNA genome sequence. Talbot et al., 1990, Nucleic Acids Research 18, No. 12, 3521–3528 have synthesised the 19 base sequence and variations of this sequence and investigated the recognition and binding by the coat protein. It has been found that not only does the translational operator RNA signal exist as the stem-loop structure within the larger genomic RNA but that it is also recognised as the short fragment of just 19 bases. This fragment has the ability to cause recombinant coat protein to bind specifically and self-assemble around it, resulting in recombinant capsids containing multiple copies of the RNA fragment.

According to the present invention there is provided a delivery system comprising capsids of the coat protein amino acid sequence of phage MS-2 or related phage, or a modification thereof which retains capsid-forming capability, or sufficient of said sequence or modification to retain capsid-forming capability, at least some of said capsids enclosing a moiety foreign to the genome of MS-2 or related phage.

The foreign moiety is suitably attached to a portion of the RNA genome sequence of MS-2 or related phage capable of functioning as a translational operator for capsid formation, or a variant thereof retaining the translational operator function. The RNA genome sequence was first defined by Fiers, Nature, 1976, 260, 500–517, and we have found that the 19-base stem loop (bases −15 to +4 relative to the start of the replicase gene) SEQ ID NO. 1 or a variant thereof, especially the variant where cytidine is substituted at the −5 position, is the minimum requirement for function as the translational operator (see Talbot et al., 1990, Nucleic Acids Research 18, No. 12, 3521–3528). The foreign moiety may be attached directly to the operator sequence or via a spacer moiety, for example a series of uridine residues (suitably 6) to ensure that the foreign moiety does not interfere with the operator function.

According to a preferred form of the invention the coat protein amino acid sequence has been modified to provide a site suitable for attachment thereto of a targeting moiety. The invention includes capsids having such a site for subsequent attachment of a targeting moiety and capsids to which the targeting moiety has already been attached.

The coat protein amino acid sequence is preferably that derived from phage MS-2, but it may also be derived from related RNA-phages capable of replication in E. coli, such as phages R17, fr, GA, Qβ and SP. Such RNA-phages of physical structure similar to that of MS-2 will contain some chemical variation in the amino acid residues of the coat protein and are thus conservatively modified variants of MS-2 coat protein. While it is believed at present that substantially the entire coat protein may be required for capsid assembly, deletions and/or insertions are also possible whilst still retaining capsid-forming capability. Proteins having such modified sequences are included within the scope of the invention.

The three-dimensional structure of the MS-2 phage particle has been published by Valegard et al., (Nature, 1990, 345, 36–41). The published data show that, firstly, the structure of the coat protein is not related to the eight-stranded β-barrel motif found in all other spherical RNA virus subunits whose structures are known at the present time. Secondly, although the coat protein exhibits quasi-equivalent inter-subunit contacts, there are no other devices, such as extended arms of polypeptide, helping to secure each protein conformer. The coat protein structure can be viewed in terms of three separate regions. These are not domains in the usual sense but could represent independent folding units. These regions are residues 1–20, which form the β-hairpin structure which protrudes from the surface of the phage forming the most distal radial feature. This region is followed by residues 21–94 which form five β-strands including the "FG-loop" which is the site of the only major conformational change between quasi-equivalent conformers. These β-strands are then followed by two α-helices, residues 95–125, which interdigitate to secure dimers of the coat protein sub-units. Valegard et al. are concerned solely with the physical structure of the MS-2 virus and do not attempt to elucidate the mode of action of the virus.

Co-pending UK patent application No. 9114003.8 describes the introduction of a cysteine residue into the N-terminal protruberant β-hairpin of the coat protein (with removal of the cysteine residues present externally of the N-terminal protruberant β-hairpin). Such a cysteine residue provides a preferred site for attachment thereto of a targeting moiety. The resultant coat protein has therefore been so modified in the region of amino acid residues 1 to 20, such numbering being with reference to the entire coat protein sequence of MS-2 as published by Fiers, Nature, 1976, 260, 500–507. Preferably the modification to introduce the cysteine residue is towards or at the middle of the hairpin region. It is preferred to introduce the cysteine in the region of the glycine 13 and 14 residues of the coat protein. The cysteine residues to be removed which are external of the β-hairpin are found at positions 46 and 101. They may be removed by any convenient conventional genetic engineering technique, suitably by site-specific mutagenesis.

In a preferred method of removing the unwanted cysteine residues, two mutants of the MS-2 coat protein, one singly mutated at cys 46 and one singly mutated at cys 101 may be obtained by standard commercially available techniques for site specific mutagenesis and the corresponding cDNA sequences introduced into standard expression vectors, which vectors are subjected to digestion with restriction enzymes to obtain separately the DNA fragment containing the mutated cys 46 site and the corresponding fragment containing the mutated cys 101 site, the fragments being subsequently ligated to give a doubly-mutated coat protein cDNA. The doubly-mutated cDNA may then be subjected to site-directed mutagenesis using standard methods to introduce a cysteine residue in the β-hairpin region.

Alternative modification of the coat protein which enables targeting of the encapsidated moiety may include insertion of peptide sequences in the protruberant β-hairpin of the MS-2 coat protein as described in co-pending UK patent application no. 9201372.1.

The cysteine residue, or alternative modification site, can be further linked to a targeting moiety with or without interposition of a further spacer moiety. An example of such a targeting moiety is a galactose residue which can be used to direct the capsids to interact with specific cell surface receptors and thus carry the foreign moiety within the capsids to and/or into specific cells. Other possible targeting moieties are other cell surface receptor ligands or monoclonal antibodies. Suitable receptors for the targeting moieties are the asialoglycoprotein receptor and the receptor for melanocyte stimulating hormone.

Suitable spacer moieties, if employed, are selected from known commercially available heterobifunctional crosslinking reagents which couple with the exposed cysteine thiol group. Examples of such cross-linkers are m-maleimidobenzoyl-N-hydroxysulfosuccinimide ester, N-succinimidyl-(4-iodoacetyl)aminobenzoate and N-succinimidyl-3-(2-pyridyldithio)propionate. The choice of crosslinker will depend on the targeting moiety and its size. Thus larger molecular species may require longer crosslinking moieties to minimise steric hindrance. The crosslinker may be linked first to the cysteine residue or first to the targeting moiety.

Alternatively the thiol function (or other derivatisable group) can be introduced into wild type, empty capsids of MS2 coat protein using suitable heterobifunctional chemical reagents such as N-succinimidyl S-acetylthioacetate (SATA).

The foreign moiety held within the capsids can vary widely and include genes and gene fragments, ribozymes, anti-sense messages or cytotoxic and chemotherapeutic agents intended for such purposes as anti-sense gene therapy or selective killing of target cells.

The form in which the foreign moiety is held within the capsids will depend on the release properties required. For release at the targeted site it will be important to ensure that the right conditions prevail, for example to permit cell localisation and internalisation via receptor mediated endocytosis.

The capsids may suitably be obtained by first obtaining empty MS-2 capsids, for example by expression of vectors containing coat protein cDNA in $E.$ $coli$ as described in co-pending UK application No. 9201372.1. The MS-2 capsids may be of wild type MS-2 coat protein or have been modified, for example to introduce a cysteine site as described in co-pending UK application No. 9114003.8. The capsids are then disassembled, for example, at acid pH (e.g. using acetic acid), before reassembly suitably at raised pH, e.g. pH 7. In the presence of the desired foreign moiety linked to an RNA sequence capable of functioning as the translational operator in the reassembly of the coat protein around the RNA sequence and foreign moiety. Other methods of disassembly may be used, for example in the presence of urea. It is also contemplated that the capsids enclosing the foreign moiety may be obtained by random incorporation of the moiety in the capsids.

The RNA sequence may be obtained by biochemical methods from the complete MS-2 RNA genome. Alternatively, the RNA sequence is obtained by chemical synthesis, for example as described by Usman et al., (1987), J. Am. Chem. Soc., 109, 7845–7854. Chemical synthesis is preferred as it enables ready addition of any spacer moiety and linking to the foreign moiety to be delivered.

It will be apparent that there are several advantages in using MS-2 and related phages as a presentation system. Thus the empty coat protein capsids can be readily expressed in comparatively high yield in $E.$ $coli$ and the product is easily purified (see R. A. Mastico et al. J. Gen. Virol. (1993) 74, 541–548 the contents of which are herein incorporated by reference). It has been found that the assembled capsids show considerable stability with respect to a range of temperatures, pH and ionic strength.

BRIEF DESCRIPTION OF THE DRAWINGS

The present invention is illustrated by the accompanying drawings, in which:

FIG. 5 represents a trace obtained from an HPLC gel filtration column described in Example C, when mixture (iii) is used;

FIG. 6 represents a trace obtained from an HPLC gel filtration column described in Example C, when mixture (iv) is used;

FIG. 7 is a graph representing the results obtained from the experiment described in Example C;

Figure 1:
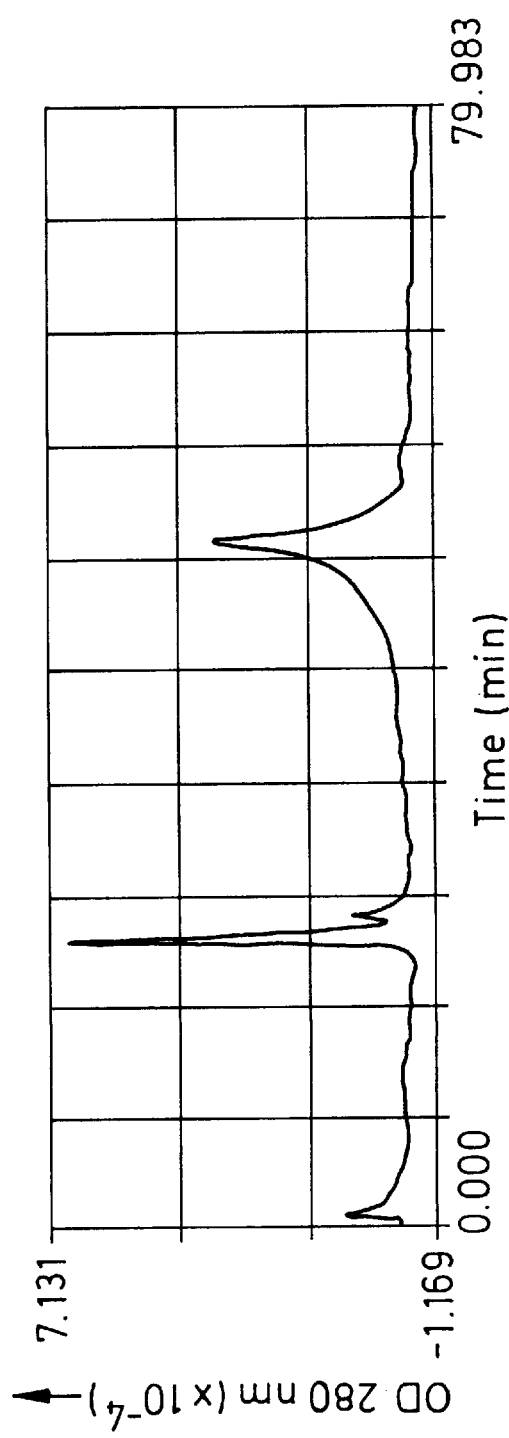
FIG. 1 represents a trace obtained from an HPLC gel filtration column described in Example C, when wild type MS-2 capsids which had not been disassembled and reassembled were used.

The invention will now be described by way of example.

A) Preparation of MS-2 Coat Protein Capsids

The coat protein of MS-2 was obtained by growing phage MS-2, purifying the RNA, followed by oligonucleotide primer directed reverse transcription to produce single-stranded cDNA which was converted to double stranded cDNA using oligo primers and Klenow polymerase. The cDNA was then subcloned into an expression vector pGL-Wll (Smith, M. C. M., Czaplewski, L. G., North, A. K., Baumberg, S. and Stockley, P. G. (1989) Mol. Microbiol. 3, 23–28,) placing the coat protein under the control of the inducible tac promoter.

The pGLWll expression vector was expressed in *E. coli* and the cellular proteins obtained, purified and characterised as follows:

Standard laboratory strains of *E. coli* were transformed (to ampicillin resistance) with the expression plasmid carrying the recombinant MS-2 coat protein gene. Rapidly growing cultures of these transformants in rich media were induced by addition of isopropyl-β-thiogalactoside (IPTG) to a final concentration of 1 mM when the $O.D._{600}$ of the culture was between 0.4–0.6. Cell growth was continued overnight before the cells were harvested by centrifugation, resuspended in neutral buffer, sonicated to lyse the cells, followed by centrifugation to separate the supernatant (containing the expressed recombinant products) and cellular debris. The supernatant was fractionated by ammonium sulphate precipitation, the pellet of product being resuspended in buffer before being purified on the basis of size by either sucrose density gradients or gel filtration chromatography or by immuno-affinity chromatography (Mastico et al. (1993)). The product was obtained in the form of capsids which were subsequently disassembled by the addition of 2 volumes of glacial acetic acid.

B) Preparation of RNA Genome Oligonucleotides

Four oligonucleotides were prepared by solid phase chemical synthesis using 2'-silyl-protected phosphoramidite starting materials as described by Usman et al., (1987), J. Am. Chem. Soc., 109, 7845–7854 and Talbot et al., (1990), Nucleic Acids Research, 18, No. 12, 3521–3528.

a) Containing nucleotides −15 to +4 of the RNA genome of MS-2 with a cytidine introduced at position −5, i.e. a sequence encompassing the translational operator (described hereinafter as "MS-2C").

b) MS-2C carrying a 5' biotin residue as a model foreign moiety;

c) As for a), but with 6 uridine residues linked at the 5' end of the oligonucleotide (described hereinafter as "MS-2C+6U") also carrying as a model foreign moiety a 5' biotin residue.

d) As for a) but with a 3' extension of 22 deoxynucleotides which are complementary, i.e. anti-sense, to the first 22 nucleotides of the mRNA for the HIV-1 Tat protein.

The biotin group in b) and c) was introduced as follows: 500 mg of "DMT biotin-C6-PA" (a dimethoxytrityl-protected biotin-C6-spacer-phosphoramidate reagent available from Cambridge Research Biochemicals Ltd., Cheshire, UK) was dissolved in 0.6 ml of anhydrous acetonitrile. The synthesis of both MS-2C+biotin and MS-2C+6U+biotin was carried out on an Applied Biosystems Model 391 DNA synthesiser on a 1 μMol scale.

Results of the syntheses with biotin:

|  | Overall Yield | Average Stepwise Yield |
| --- | --- | --- |
| MS-2C + biotin | 62.4% | 97.5% |
| MS-2C + 6U + biotin | 38.9% | 96.2% |

The solid supports from all four syntheses were transferred into clean vials and treated with HPLC grade methanol saturated with ammonia for 24 hours at room temperature. The supernatants were transferred to fresh vials and dried down using a stream of nitrogen gas.

The resulting pellets were then resuspended in t-butylammonium fluoride in THF, and incubated at room temperature for 24 hours, and then quenched using an equal volume of 1M ammonium acetate.

The quenched deprotection reactions were then desalted using Pharmacia NAP 25 columns. The columns were equilibrated with 25 mls 0.2× TBE and 2.0 mls of sample was added to the columns, with 0.5 ml fractions being collected. Once all the material had been eluted, the columns were re-equilibrated as before and the second half of the sample was desalted likewise. A fresh column was used for each RNA oligonucleotide.

The size of each product was confirmed by 3' radiolabelling and chromatography over polyacrylamide sequencing gels. Auto radiography recorded single dominant radioactive species with expected mobilities.

C) Reassembly of Capsids in the Presence of Oligonucleotide-Biotin and MS-2C-Anti-Tat Reassembly of the disassembled MS-2 capsids described in A) above was carried out by raising the pH from 2.4 to 7.0 in the following circumstances and in each case in the presence of an avidin-fluorescein complex (Pierce Europe BV, Holland).

i) MS-2 coat protein only (no oligonucleotide present)

ii) MS-2 coat protein plus MS-2C iii) MS-2 coat protein plus MS-2C+6U-biotin iv) MS-2 coat protein plus MS-2C-biotin.

Figure 2:
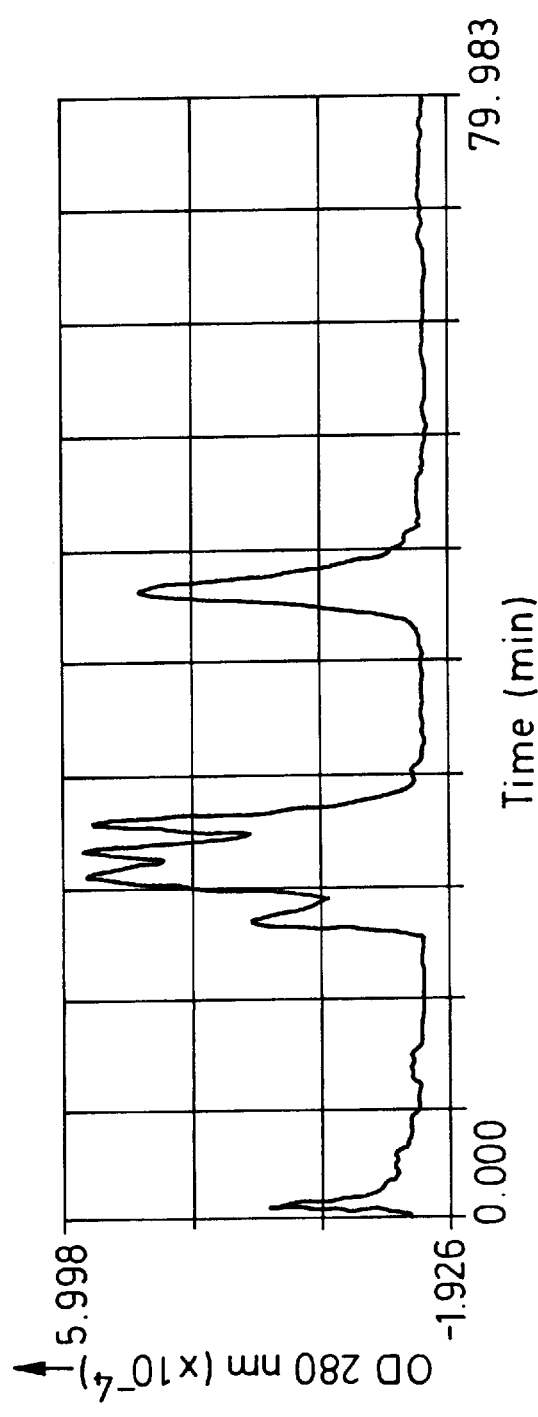
FIG. 2 represents a trace obtained from an HPLC gel filtration column using molecular weight standards.

The resulting capsids were separated on an HPLC gel filtration column and the results are shown in FIGS. 1 to 6 where FIG. 1 represents the trace obtained using wild type MS-2 capsids which had not been disassembled and reassembled and FIG. 2 represents molecular weight standards. The peak eluting after approximately 19 minutes corresponded to the assembled MS-2 capsids. FIGS. 3 to 6 represent the traces obtained for the mixtures i), ii), iii) and iv) respectively. It will be seen that while i) shows only a small indication of capsid formation, ii) shows a greatly increased amount of capsid as expected while iii) and iv) show retained capsid formation in the presence of avidin-fluorescein which will complex with the biotinylated oligonucleotides.

Figure 3:
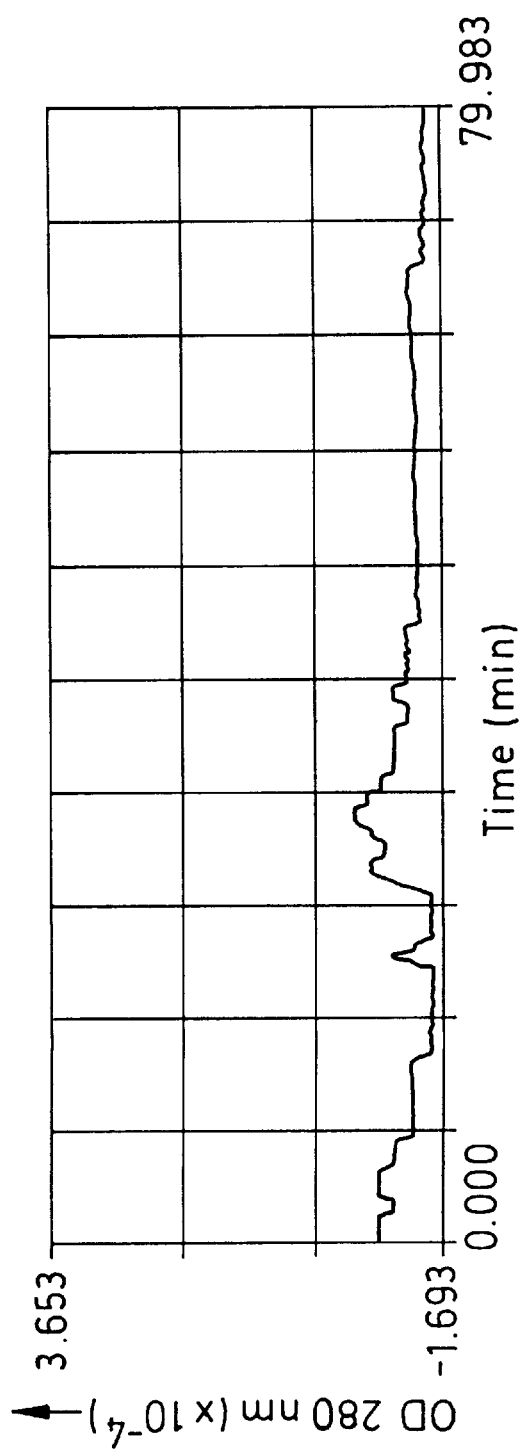
FIG. 3 represents a trace obtained from an HPLC gel filtration column described in Example C, when mixture (i) is used.
Figure 4:
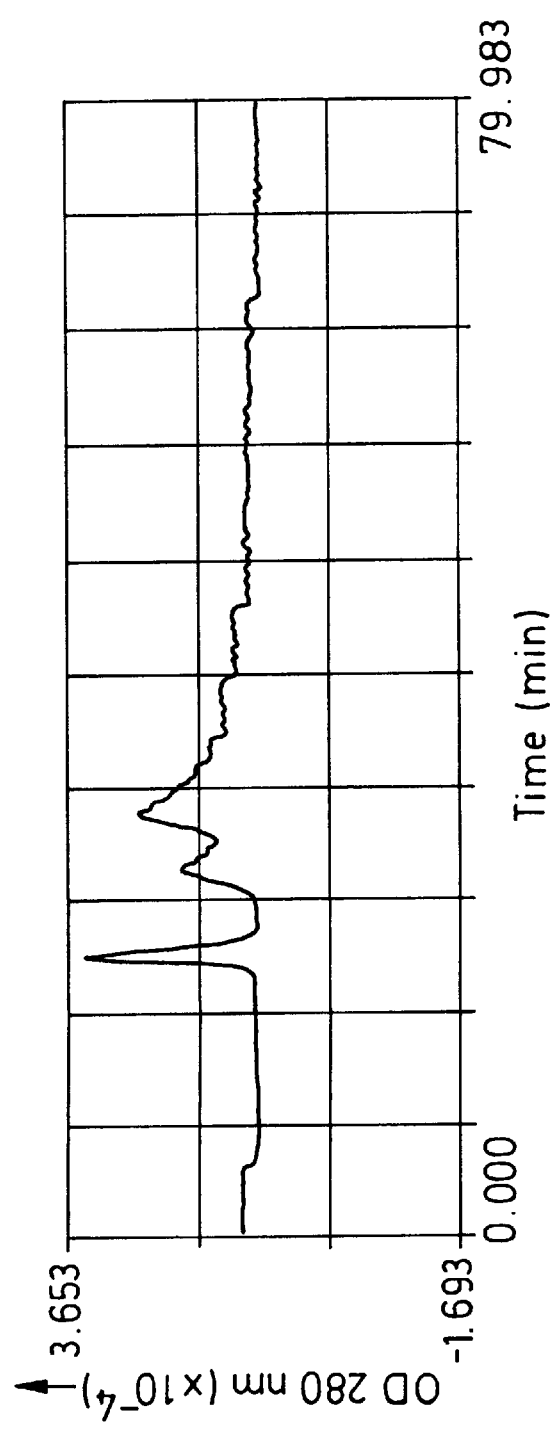
FIG. 4 represents a trace obtained from an HPLC gel filtration column described in Example C, when mixture (ii) is used.

The presence of the avidin-fluorescein-biotin complex within the capsids was demonstrated by measuring the fluorescence intensity (resulting from fluorescein) in the fractions corresponding to the capsid peaks in FIGS. 3, 4 and 5 (i.e. for i), ii) and iii) above) plus additionally a mixture:

v) MS-2 coat protein plus 1:1 mixture of MS-2C+6U-biotin and MS-2C (no biotin) plus avidin-fluorescein complex.

The results are shown in FIG. 7 and it will be seen that iii) showed the presence of fluorescence in the fractions corresponding to the capsids while v) showed the presence of a reduced level of fluorescence when the biotinylated oligonucleotide was diluted 1:1 with non-biotinylated oligonucleotide. The avidin-biotin complex is thus shown as being within the capsids.

MST WT capsids are reassembled with the (MS-2C-anti-Tat) as follows:

a) Reassembly

MS2 WT CP was purified as usual, but concentrated to 10 mg/ml by spinning down at 35 k rpm for 6 h at 4° C. 0.4 ml of the MS2 (10 mg/ml) was added to 0.8 ml of glacial acetic acid and kept on ice for 30 min. The precipitates were removed by centrifugation at 6500 rpm, 4° C. for 20 min and the supernatant passed over a NAP-25 column equilibrated with 1 mM acetic acid. Both the protein and the oligonucleotide were mixed with 10× TMK buffer (100 mM Tris, 80 mM KCl and 10 mM $MgCl_2$) and kept on ice for 1 h. The MS2 CP was added to the MS-2C-anti-TAT solution at molecular ratios from 180:1 to 2:1 and the mixture incubated at 37° C. for 1 h and then RT for 6 h. The reassembled capsids were stable at 4° C. for 2 weeks.

b) Analysis of the Reassembled Capsids

In order to confirm that the reassembled particles had encapsidated the test oligonucleotide capsids were separated from other components by HPLC gel filtration chromatography as described above. The peak corresponding to capsids was then phenol extracted, the nucleic acids precipitated with ethanol, the precipitate radiolabelled with $^{32}P$ and electrophoresed over a denaturing polyacrylamide gel. The results showed that a nucleic acid fragment with identical mobility to the starting material had been recovered from the HPLC column confirming encapsidation. Finally, we used transmission electron microscopy (as described above) to investigate the reassembled particles. This showed that the bulk of the input coat protein had reassembled into capsids of similar size and symmetry to the wild type phage.

C) Eukaryotic Cell Transfection

Human Hela cells were grown in Dulbecco modified Eagle medium supplemented with 10% fetal calf serum. Twenty four hours before transfection the cells were plated out at $1 \times 10^6$ cells per 75 $cm^2$ flask. The medium was changed half an hour before the transfection.

The cells were transfected with 5 μg LTR Cat and 5 μg pSVTat (1) in 0.5 ml of calcium phosphate-DNA coprecipitate (2). After 16 hours the cells were washed with PBS and fresh medium was added. The cells were then incubated for 24 hours before harvesting. The transactivation of LTRCat by Tat was challenged with the antisense oligo directed against the first 22 bases of the Tat mRNA. This was attached to the 3' end of the MS2 RNA stem loop (−15 to +4) to direct the reassembly of the capsid around the oligo.

The ser 46 single mutant from step A) was introduced into standard coat protein expression vector ptacACP and digested with SacI and XbaI restriction enzymes and the longer backbone fragment so obtained treated with calf intestinal phosphatase and then purified on agarose or polyacrylamide gels before electroelution and precipitation.

The ser 101 mutant was treated likewise with omission of the phosphatase treatment. The smaller fragment containing the C-terminal portion of the coat protein gene was purified by gel electrophoresis.

The large fragment containing the mutated cys 46 site and the small fragment containing a mutated 101 site were ligated by standard methods. The recombinant molecules thus obtained were used to transform *E. coli* TG1 to ampicillin-resistance and positive colonies checked for double mutation by DNA sequencing.

The doubly-mutant ser 46/101 coat protein cDNA from step B was introduced into an M 13 sequencing vector by standard subcloning methods, a single stranded template for site-directed mutagenesis generated and a cysteine residue introduced at gly 14 using the commercially available site specific mutagenesis protocol based on nucleotide phosphothioates. There was thus obtained mutated cys 14 Ser 46/101 coat protein cDNA.

The isolated mutated cDNA was expressed in *E. coli* to confirm the capsid-forming ability of the recombinant protein. The cys 14 ser 46/101 coat protein cDNA of C) above was introduced to expression vector pTAC-CP and the resultant plasmid used to transform *E. coli* strain TG1 in accordance with standard procedure. The cys 14 ser 46/101 coat protein was then produced according to the following protocol.

5×5 ml (2TY media with 100 μg/ml ampicillin) cultures of single colonies picked from transformation plates were grown for approx. 4 hrs at 37° C. and then used to inoculate 5×500 ml flasks of 2TY plus ampicillin and the cultures were grown at 30° C. When the cultures reached $OD_{600}$ approx. 0.45 protein production was induced by adding 1 mM IPTG. Cells grown overnight were then centrifuged at 3 k rpm, 30 mins, 4° C. in a Beckman JA14 rotor.

The resulting pellets were resuspended in 50 mM Hepes, 100 mM NaCl, 10 mM dithiothreitol (DTT), 5 mM EDTA and 1 mM phenylmethyl sulphonyl fluoride (PMSF), and the cells lysed by sonication. The cell lysate was then centrifuged at 15 k, 20 mins, 4° C. in a Beckman JA20 rotor and the supernatant passed down a NAP-25 column (Pharmacia) to change buffers to 20 mM NaPi (sodium phosphate-based buffer) pH 7.0. 1 ml fractions were collected from the NAP column, the MS-2 coat protein containing fractions (nos. 2 to 5 inclusive) added to an anti-MS-2 coat protein immunoaffinity column and the sample allowed to bind for 1 hour at room temperature with gentle agitation.

(5'-ACA-UGA-GGA-UUA-CCC-AUG-U--TAC-CTC-GGT-CAT-CTA-GGA-TTG-3') SEQ ID NO:2

D) Preparation of Cysteine or Thiol-Modified Coat Protein Capsids

Cystene modified MS-2 coat protein was produced as follows:

Site directed mutagenesis and standard techniques were used to produce amino acid mutants at coat protein positions 46 and 101.

Mutants were selected having either cysteine at position 46 substituted by serine or cysteine at position 101 substituted by serine.

Each single mutant DNA was expressed in *E. coli* to demonstrate the ability to self assemble.

The column was washed with 20 mM NaPi pH 7, then 10 mM NaPi/100 mM NaCl pH 7. The sample was eluted with 20 mls 20 mM acetic acid/200 mM NaCl approx. pH 2.7 and the first 4 mls collected.

The pH was immediately adjusted by titration with 1M Tris.HCl pH 9 to pH 7–7.4 and the mixture centrifuged at 30 k rpm, 4° C. overnight (approx. 15 hrs) using a Beckman SW.55Ti rotor. The supernatant was decanted and the MS-2 protein pellet resuspended in a small volume of the required buffer.

Homogenous cys 14 modified capsids were obtained which were tested for their ability to react with an activated galactose reagent as described in E) below.

Figure 8:
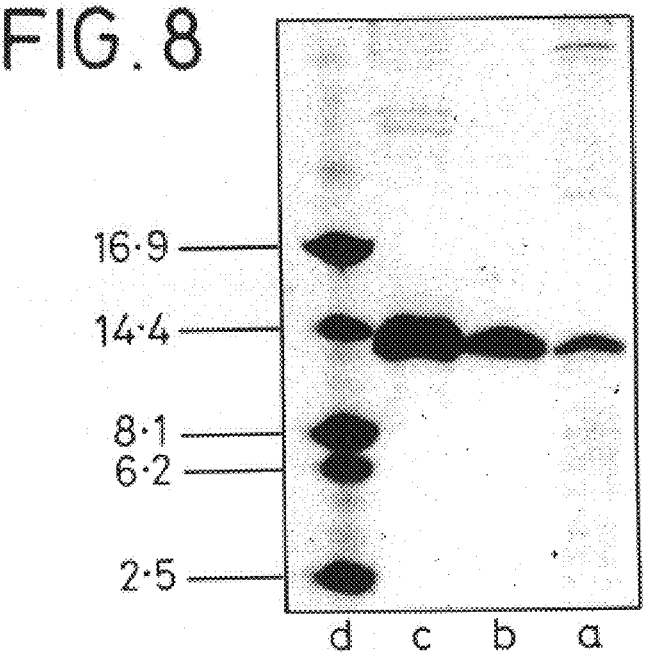
FIG. 8 is an SDS-Page gel of cys 14 modified MS-2 capsid.

SDS-PAGE of the resultant immunoaffinity purified cys 14 modified capsids showed essentially a single component of the expected molecular weight. This result is shown in FIG. 8 where lane a) shows the cys 14 modified capsids, lanes b) and c) show wild type capsids respectively immunoaffinity purified and sucrose density purified and lane d) gives molecular weight standards.

Figure 9:
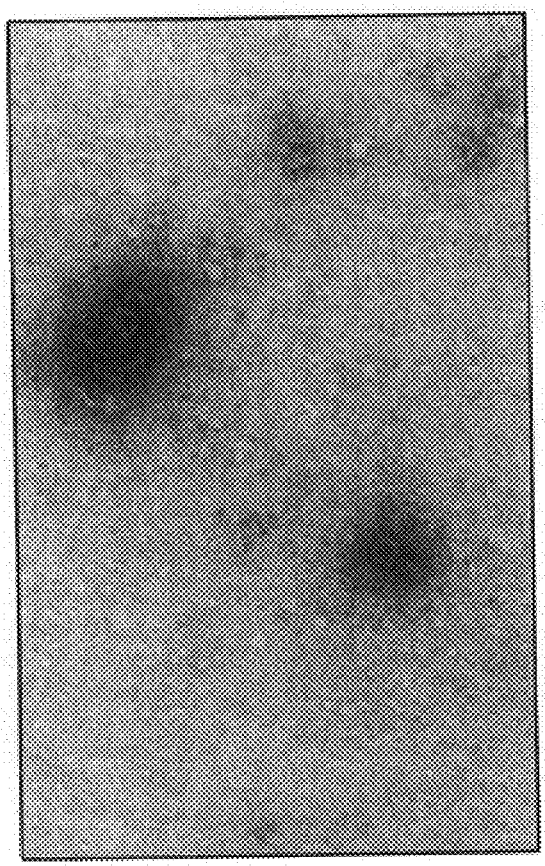
FIG. 9 is an electromicrograph of the immunoaffinity purified cys 14 modified MS-2 capsid.

FIG. 9 shows an electromicrograph of the immunoaffinity purified cys 14 modified capsids showing the presence of assembled particles similar to those produced by wild type coat proteins.

Thiol groups can also be introduced into wild type assembled capsids using heterobifunctional reagents such as SATA, as follows:

2 mg of N-succinimidyl S-acetylthioacetate (SATA, Pierce Immunotechnology) was completely dissolved in 0.5 ml of dimethylformamide (DMF) by shaking, and 20 µl aliquots stored at 4° C. The purified MS2 WT CP was passed over a NAP-25 column equilibrated with 0.05M phosphate buffer (PB,pH7.5) immediately before conjugation. 1 ml of MS2 CP (1 mg/ml) was mixed with 20 µl of SATA and kept at RT for 1 h (SATA:MS2=50:1). The solution was then deacetylated with 0.1 ml of freshly prepared hydroxylamine-HCl (25 mg in 0.5 ml $H_2O$) at RT for 2 h. The MS2 derivative was separated from the reagent and by-products by desalting over a NAP-25 column equilibrated in 0.1M PB pH7.5.

The stoichiometry of SATA groups introduced into wild type MS2 coat protein was determined either by modification with DTNB (as described below) or $^3$H-iodo-acetic acid according to standard methods. The results suggest that approximately two new thiols per CP monomer are introduced by the SATA modification. Both new thiols were completely modified by treatment with activated galactose, as described below.

E) Reaction of Cysteine or SATA Modified Protein With Activated Galactose

In order to test the reactivity of the cys 14 modified MS-2 capsids, a halogen-activated galactose was prepared as follows:

To a stirred solution of p-aminophenyl β-D-galactopyranoside (0.54 g; 2 mmole) in water (4 ml) and ethanol (6 ml) was added iodoacetic anhydride (0.9 g; 2.5 mmole) at room temperature. After 2 hours, the reaction was concentrated to dryness and the residue washed with ether (2×10 ml). Crystallisation from ethanol gave the product as needles (0.7 g; 80%), mp 158–160° C.

Figure 10:
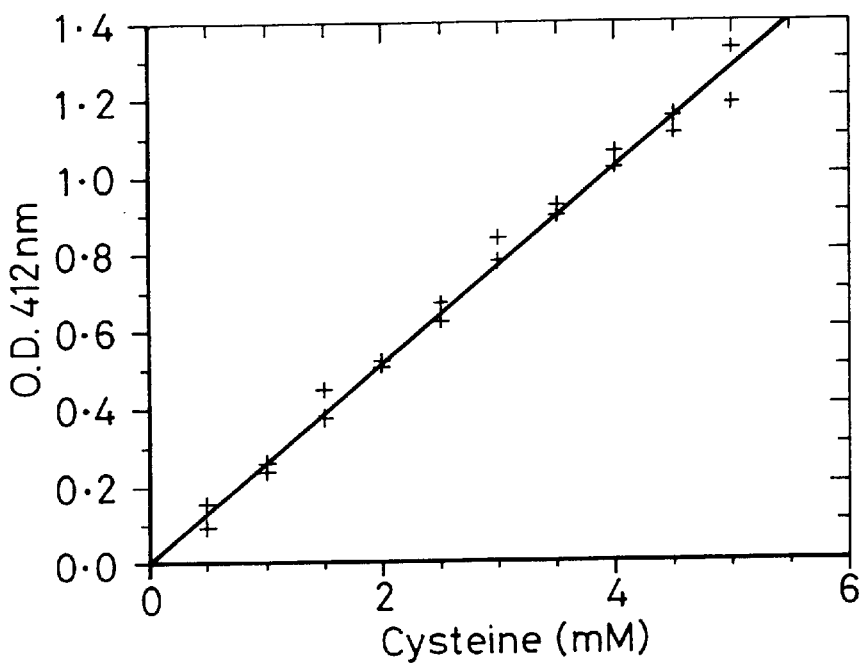
FIG. 10 shows a control curve for reaction of free cysteine with DTNB, as described in Example E, on page 15.

The reaction of the cys 14 modified capsids with the activated galactose was assayed using Ellman's reagent (dithionitrobenzoate, DTNB) which gives a characteristic absorption at $OD_{412}$ on reaction with free —SH groups. FIG. 10 shows a control curve for reaction of free cysteine with DTNB. The control curve was obtained using:

100 µl sample.

100 µl DTNB 4 mg/ml in 100 mM $Na_2HPO_4$ pH8 ("buffer 1").

5 ml "buffer 1".

The mixture was left at room temperature for 15 minutes after adding DTNB and then the $OD_{412}$ recorded.

Figure 11:
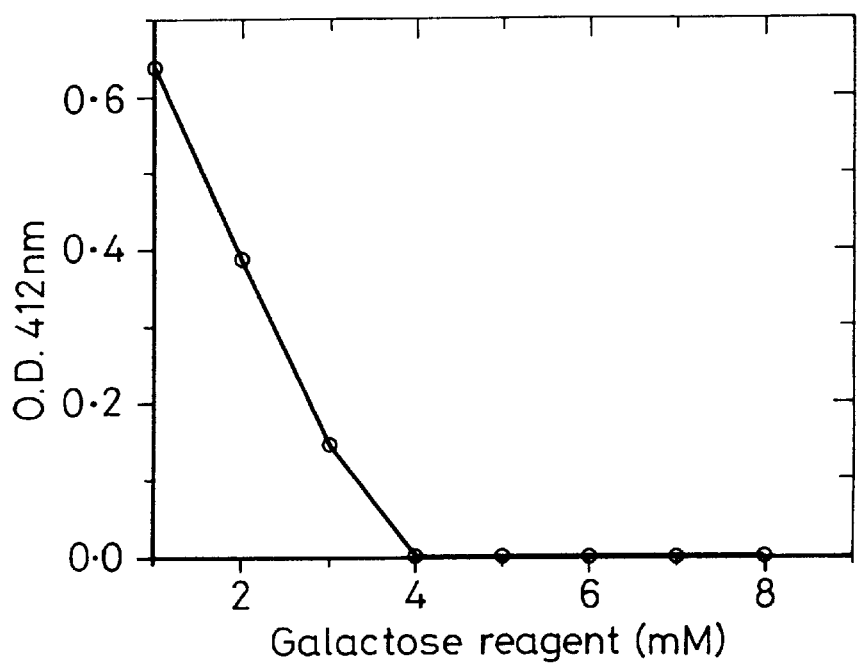
FIG. 11 shows the curve obtained when cysteine was mixed with 1 to 10 mM activated galactose and left to stand at room temperature for 1 hour, followed by assay using DTNB, as described in Example E.

FIG. 11 shows the curve obtained when cysteine (4 mM) was mixed with from 1 to 10 mM activated galactose and left to stand at room temperature for 1 hour, followed by assay of these 100 µl aliquots as described above using DTNB.

The cys 14 modified coat protein was reacted with DTNB as follows:

Purified cys 14 modified capsids were resuspended in buffer 1 containing 1 mM EDTA to a final concentration of 400 µg/ml. The following individual experiments were set up.

1) 100 µl protein sample, 100 µl 5 mM activated galactose.
2) 100 µl protein sample, 90 µl buffer 1, 10 µl 5 mM activated galactose.
3) 100 µl protein sample, 100 µl buffer 1.

Each was left stirring at room temperature for 1 hour before addition of 200 µl DTNB 4 mg/ml in ethanol to the stirring solution. $OD_{412}$ was recorded after 15 minutes and the results are shown in Table 1 below. The number of free thiols decreased with increasing exposure to the galactose reagent, confirming that the cys 14 capsids had been derivatised with galactose. Similar results were obtained with SATA—modified wild-type capsids.

TABLE 1

| Sample | $O.D._{412\ nm}$ |
|---|---|
| Buffer blank | 0.0 |
| 1) 100 µl MS2-cys; 100 µl gal | 0.031 |
| 2) 100 µl MS2-cys; 90 µl buffer; 10 µl gal | 0.080 |
| 3) 100 µl MS2-cys; 100 µl buffer | 0.118 |

F) Linking of cys 14 Modified Coat Protein to Immunogenic Peptide

The purified cys 14 modified capsids were linked as described below to HA10, a 10-mer peptide sequence encompassing a nonapeptide epitope derived from the haemagglutinin of the human pathogen influenza virus and having an N-terminal cysteine residue extension, which 9-mer sequence YPYDVPDYA (SEQ ID NO:3) has been identified as containing one of the antigenic determinants by Wilson et al., Molecular and Cell Biology, May 1988, 2159–2165 and Cell, 37, 1984, 767–778. The procedure involved an initial crosslinking step to form a disulphide linkage which was then oxidised.

The following reagents were employed to make up four test reaction mixtures:

2 µg cys 14 modified capsids (about 3 µl ) ("cys bridge")
1 µl 1M Tris.HCl pH8, 10 mM EDTA ("buffer 2")
17 µg HA9 peptide (about 2 µl) ("peptide")
1 µl 2-mercaptoethanol ("βME")

The following four test mixtures were prepared, in each case made up to 10 µl with water:

1) cys bridge+buffer 2+βME
2) cys bridge+buffer 2
3) cys bridge+buffer 2+βME+peptide
4) cys bridge+buffer 2+peptide The mixtures were incubated for 1 hour at room temperature. There was then added 1 µl of a mixture of 0.37M sodium tetrathionate and 1.6M sodium sulphite (which had been freshly prepared in accordance with the method of Morehead et al., Biochem., 23, 1984, 2500). The mixtures were left overnight at room temperature.

The mixtures were analysed using a PAGE Schägger System (Schägger et al., 1987, Anal. Biochem., 166, 368–379), blotted onto nitrocellulose paper using a Bio-Rad Western blotting apparatus, with a transfer buffer of 39 mM glycine, 48 mM Tris, 0.1% (w/v) sodium dodecyl sulphate (SDS) and 20% methanol for a transfer time of 1 hour at 450 mA.

The blots were washed with phosphate buffered saline (PBS) pH 7.6 containing Tween 20 (polyoxyethylene sorbitan monolaurate—3 ml per liter PBS) to equilibrate. They were then incubated for 1 hour at 37° C. with 35 ml PBS-Tween plus 0.5% (w/v) bovine serum albumin (BSA), washed 6×5 min. with 200 ml PBS-Tween and subsequently incubated overnight at 4° C. with 35 ml PBS-Tween+0.5% (w/v) BSA together with 100 µl mouse anti-HA9 monoclonal antibody (obtained from Balcore Co., Berkley, U.S.A.). There then followed washing with PBS-Tween (6×5 min.—200 ml) and incubation for half an hour with 35 ml PBS-Tween+0.5% (w/v) BSA together with 50 µl goat anti-mouse IgG horseradish peroxidase (HRP) conjugate. After further washing (6×6 min.—200 ml PBS-Tween), the gel was excited by luminol Western blotting reagents (Amersham) and visualised.

The results showed that only a single band in the lane corresponding to sample number 4 cross-reacted with the anti-HA9 antibody. This is the expected result, samples 1–3 being negative controls. Thus it is possible to couple linear peptide fragments to cys 14 capsids using these methods.

G) Covalent Cross-Linking of cys 14 Modified Coat Protein to an Enzyme or Targeting Ligand Protein The purified cys 14 modified capsids described in E) above were covalently linked via a maleimide group to the enzyme horseradish peroxidase (HRP) as follows:

HRP-maleimide conjugate (Pierce Europe BV, Holland), cys 14 modified capsids and βME were used to make the following mixtures, each of which was made up to 100 µl with 100 mM NaPi, pH 7.2:

1) 20 µg HRP-maleimide plus 1 µl βME 2) 20 µg cys 14 modified capsids plus 1 µl βME 3) 20 µg cys 14 modified capsids plus 20 µg HRP-maleimide Sample 3) was left for 1 hour at room temperature and then βME added to quench any remaining thiols. Samples 1–3 were then fractionated by HPLC gel filtration chromatography on PW 3000, 2×30 cm columns, in 100 mM NaPi, pH 7.2 at a flow rate of 0.5 ml/min. Fractions (1 min.—0.5 ml) of the eluate were then assayed for HRP activity using the commercially available kit (ABTS reagent, Pierce), enzyme activity being estimated by observing the increased absorbance of solutions at 410 nm. The data showed a significant increase over background levels in fractions corresponding to the $OD_{280}$ peak of cys 14 assembled material of sample 3.

H: Coupling of SATA-modified MS2 WT CP to maleimide-activated HRP.

Maleimide-activated HRP was purchased from Pierce at a concentration of 1 mg/ml. 1 ml of SATA-modified MS2 was reacted with 0.1 mg HRP at RT for 6 h and then transferred to 4° C. for storage. Samples passed over HPLC gel filtration columns were analysed to determine the efficiency of the conjugation by both enzyme assay for HRP and Western Blots with anti-CP antibodies, which were consistent with formation of a covalent cross-link between the capsid and HRP.

I: Coupling of SATA-modified MS2 WT CP to maleimide-activated transferrin (TF).

MS2 was modified with SATA using the same methods as described above. TF was then activated for reaction as follows: 1 mg of transferrin (TF) was dissolved in 0.5 ml of 0.05M PB, pH7.5, and 0.5 mg of Sulfosuccinimidyl 4-(N-maleimidomethyl)cyclohexane-1-carboxylate (Sulfo-SMCC) dissolved in 30 µl of PB, and then the two solutions were mixed and kept at 37° C. for 30 min with gentle shaking. The precipitates were removed by spinning at 3 k rpm for 10 min at 4° C. and the supernatant passed over a NAP-25 column equilibrated in 0.05M PB.

Conjugates were made as follows: 1 ml of MS2-SATA (0.75 mg/ml) was added to 1 ml of maleimide-activated TF (0.44 mg/ml) in a solution flushed with nitrogen gas and kept at RT for 6 h then stored at 4° C. Conjugates appeared stable over a period of at least one month at 4° C. The samples were analysed by HPLC chromatography and Western blotting with both anti-CP and anti-transferrin antibodies, as described above. The results confirmed formation of covalent cross-links between the capsids and transferrin.

H) Cell Entry of MS-2

Figure 12:
FIG. 12 shows macrophage sections negatively stained, as described in Example H.
Figure 13:
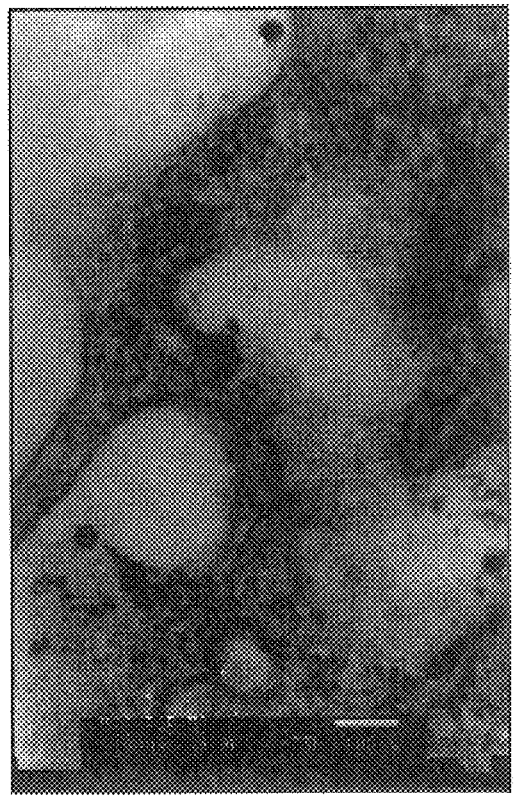
FIG. 13 shows macrophage sections negatively stained, as described in Example H.
Figure 14:
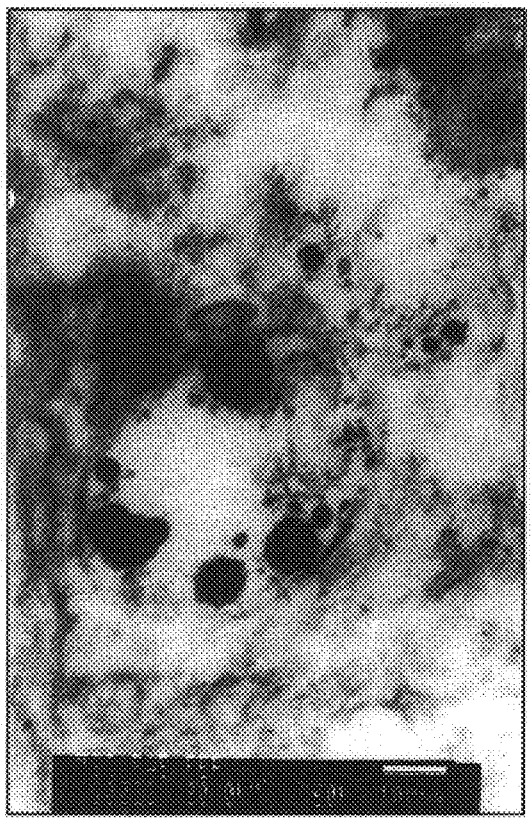
FIG. 14 shows macrophage sections treated with anti-rabbit peroxidase, which then stains the anti-MS-2 antibodies, as described in Example H.
Figure 15:
FIG. 15 shows macrophage sections treated with anti-rabbit peroxidase, which then stains the anti-MS-2 antibodies, as described in Example H.

Wild type recombinant MS-2 RNA-empty capsids prepared as described in A) above were allowed to react with rabbit polyclonal anti-MS-2 serum and then incubated for one hour with mouse macrophages. The macrophages normally function by binding to Fc portions of immunocomplexes via a cell surface receptor which is then endocytosed. The experiment thus sought to demonstrate cell entry of MS-2 particles via endocytosis. The results were analysed by embedding the macrophage cells in a plastic block followed by thin sectioning and various staining procedures. The results are shown in FIGS. 12 to 15. FIGS. 12 and 13 show macrophage sections negatively stained. 300 Å particles (MS-2 capsids) can clearly be seen in essentially all the sections viewed. FIGS. 14 and 15 show similar sections which have been treated with anti-rabbit peroxidase which then stains the anti-MS-2 antibodies (black dots in photograph). Both 300 Å and larger aggregates are heavily stained and in the last panel the staining is clearly dispersing within the cell as would be predicted following dissociating of the complex in the lysosome.

What is claimed is:

1. A delivery system comprising a capsid formed from a coat protein of a bacteriophage selected from the group consisting of MS-2, R17, fr, GA, Qβ, and SP and a foreign moiety enclosed in the capsid, wherein the foreign moiety is of a size sufficiently small to be enclosed in the capsid and wherein the foreign moiety is linked to a RNA sequence comprising a translational operator of the bacteriophage, which translational operator binds to the coat protein during formation of the capsid.

2. The delivery system of claim 1, wherein the bacteriophage is MS-2 or R17 and the RNA sequence comprises the sequence of SEQ ID NO:1.

3. The delivery system of claim 2, wherein the base position at 11 of the sequence of SEQ ID NO:1 is replaced with cytidine.

4. The delivery system of claim 1, wherein the foreign moiety is linked directly to the RNA sequence.

5. The delivery system of claim 1, wherein the foreign moiety is linked to the RNA sequence through a spacer moiety.

6. The delivery system of claim 1, wherein the N-terminal protuberant β-hairpin of the coat protein of the capsid has been modified to provide a site suitable for attachment thereto of a targeting moiety.

7. The delivery system of claim 6, wherein the site is a cysteine residue.

8. The delivery system of claim 6, wherein a targeting moiety is directly attached to the coat protein or linked to the coat protein through a spacer moiety.

9. The delivery system of claim 8, wherein the targeting moiety comprises galactose.

10. The delivery system of claim 1, wherein the foreign moiety is selected from the group consisting of a gene, gene fragment, ribozyme, anti-sense oligonucleotide, cytotoxic agent and chemotherapeutic agent.

11. The delivery system of claim 1, wherein the bacteriophage is GA.

12. The delivery system of claim 1, wherein the bacteriophage is Qβ.

13. The delivery system of claim 1, wherein the bacteriophage is SP.

14. The delivery system of claim 1, wherein the bacteriophage is fr.

15. A method of preparing a delivery system of claim 1, comprising:

providing the foreign moiety;

linking the foreign moiety to the RNA sequence to produce the foreign moiety linked to the RNA sequence;

providing the capsid; and incorporating into the capsid the foreign moiety linked to the RNA sequence, such that the capsid encloses the foreign moiety.

16. The method of claim 15, wherein the foreign moiety linked to the RNA sequence is incorporated into the capsid by disassembly of the capsid at acid pH in the presence of the foreign moiety linked to the RNA sequence followed by reassembly of the capsid at an increased pH.

* * * * *

SEQUENCE LISTING

<160> NUMBER OF SEQ ID NOS: 3

<210> SEQ ID NO 1
<211> LENGTH: 19
<212> TYPE: RNA
<213> ORGANISM: Phage MS-2

<400> SEQUENCE: 1
acaugaggau uacccaugu                                                19

-continued

```
<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence:  Phage
                        MS-2 translational operator RNA conjugated to
                        antisense oligonucleotide directed against Tat
                        mRNA

<400> SEQUENCE: 2
acaugaggau uacccaugut acctcggtca tctaggattg                              40

<210> SEQ ID NO 3
<211> LENGTH: 9
<212> TYPE: PRT
<213> ORGANISM: Human influenza virus

<400> SEQUENCE: 3

Tyr Pro Tyr Asp Val Pro Asp Tyr Ala
 1               5
```